United States Patent
Junkel et al.

[11] 3,935,761
[45] Feb. 3, 1976

[54] DENTAL HANDPIECE WRENCH

[75] Inventors: Wolfgang O. Junkel, Mount Prospect, Ill.; Jeffrey M. Kneipper, Kenosha, Wis.

[73] Assignee: American Hospital Supply Corporation, Evanston, Ill.

[22] Filed: Feb. 19, 1975

[21] Appl. No.: 551,006

[52] U.S. Cl. ............................................. 81/55
[51] Int. Cl.² ..................................... B25B 1/00
[58] Field of Search .................. 81/55, 56; 32/27

[56] References Cited
UNITED STATES PATENTS

| | | | |
|---|---|---|---|
| 3,323,395 | 6/1967 | Burnett et al. | 81/55 |
| 3,325,899 | 6/1967 | Staunt | 32/27 |
| 3,394,623 | 7/1968 | Kinakin | 81/55 |
| 3,888,008 | 6/1975 | Lake et al. | 32/27 |

*Primary Examiner*—James L. Jones, Jr.
*Attorney, Agent, or Firm*—Dawson, Tilton, Fallon & Lungmus

[57] ABSTRACT

An improved chuck wrench for contra-angle dental handpieces. The wrench includes a unitary angular C-shaped body, one of the arms of the body being provided with a socket and recess for accurately locating the wrench in position relative to the head of a handpiece when chuck adjustment (or removal) is desired. Between the paired arms is a knurled cylindrical wheel dimensioned to fit comfortably between, and be rotated by, the same fingers that receive the narrower connecting portion of the C-shaped body. A torsion spring shaft extends through the wheel and into the socket and has a non-circular end portion receivable within an opening of a handpiece chuck for locking the two parts (chuck and shaft) against independent relative rotation. A shoulder of the shaft limits the extent that the end portion may be inserted into the chuck opening, and the substantial length of that shaft, and its relationship with the other parts of the wrench, result in a torsional flexure of the shaft upon chuck tightening that signals the user when the torque limit is approached. The shaft, as well as the tangs which engage the burtube of the handpiece during an adjustment operation, are spring-loaded for limited axial movement.

25 Claims, 11 Drawing Figures

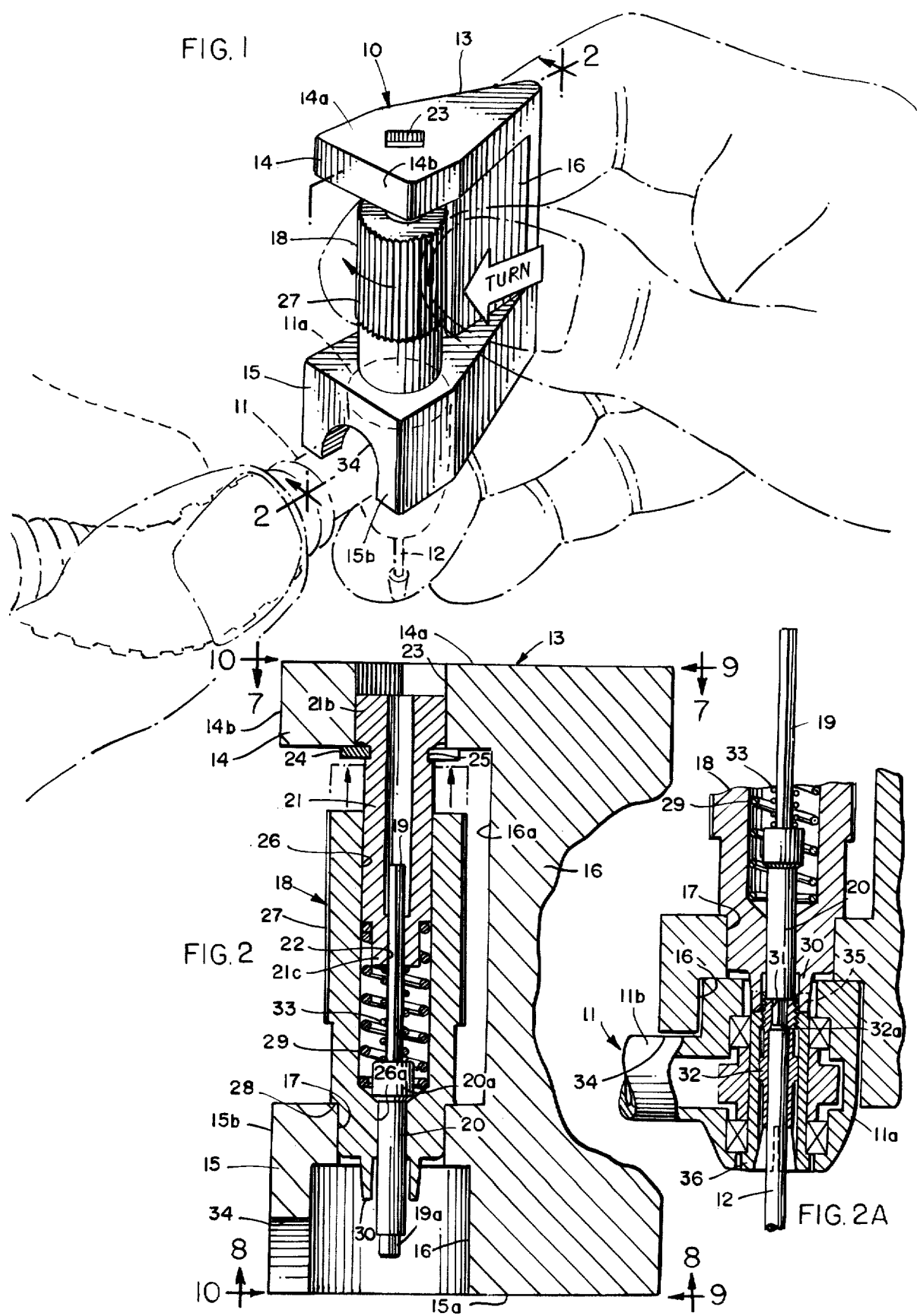

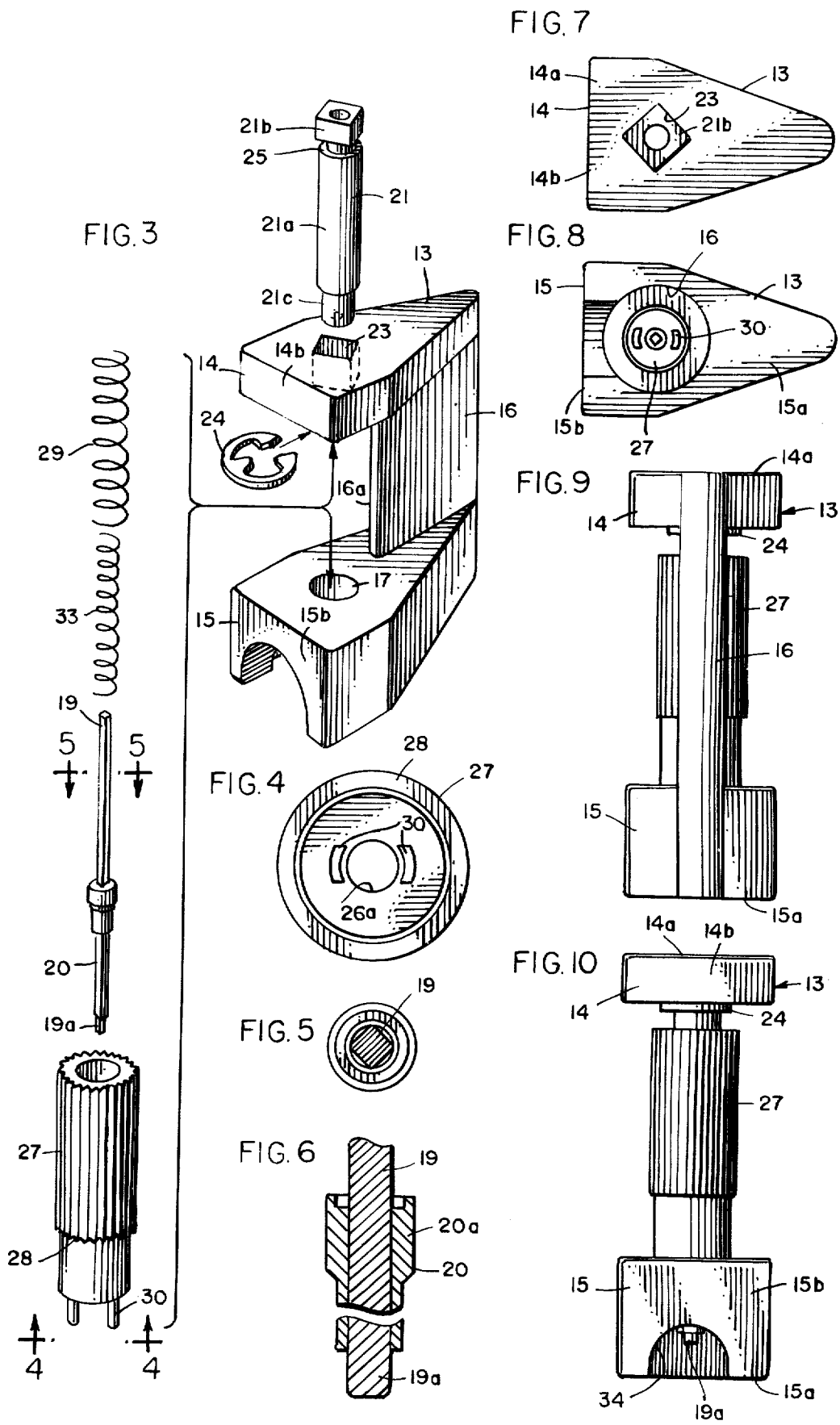

DENTAL HANDPIECE WRENCH

BACKGROUND

Co-owned co-pending application Ser. No. 326,569, filed Jan. 24, 1973, now U.S. Pat. No. 3,888,008, discloses handpiece wrenches which may be attached to contra-angle handpieces and then manipulated to adjust, or even remove, the chucks of those handpieces. In each of the disclosed forms, the wrench locks the chuck against rotation while at the same time coupling the burtube or rotor to a knurled wheel which is then rotated to turn the burtube and thereby release or tighten the jaws of the chuck. While such construction is highly effective if properly operated, there is a possibility that careless manipulation, or operation by an uninformed or misinformed user, could result in damage to the relatively delicate and precisely fitting parts of the handpiece.

The same is true with regard to the operation of earlier constructions such as the one described in co-owned U.S. Pat. No. 3,325,899. In that construction, the chuck adjustment is performed by a wrench which holds the rotor (burtube) against rotation while permitting rotation of the chuck as one section of the wrench is turned.

With regard to these and other prior art constructions, poor technique in the operation of the wrenches can result in overtightening, jamming, and breakage. In some cases, additional difficulties have been presented because manipulation of the wrenches has resulted in inadvertent partial displacement of the burs, which in turn may cause imbalance, accelerated wear, and unintentional loosening or release of the bur, or because alignment of the mating parts of the wrenches and handpieces has required considerable care to avoid damage to the handpieces. Problems of alignment might appear to have been reduced by those constructions in which the wrenches are provided with sockets that receive portions of the handpieces and serve as guides to locate the wrenches; however, in such constructions there is the further danger that since the shafts and tangs (or lugs) are shrouded from view, misalignment difficulties, although perhaps less frequent, may be more serious. Thus, if such a wrench is canted at the time that the handpiece head is forced into the socket, there is a danger that rotation of the operating wheel of such a wrench will cause the tangs of that wrench to damage that portion of the burtube provided with recesses for receiving such tangs.

SUMMARY

This invention is concerned with a wrench construction which overcomes or greatly reduces the aforementioned problems. The wrench is relatively simple to use and, because of its construction, the possibilities of accidental damage to a handpiece because of hasty or inexperienced operation are greatly reduced.

The configuration of the wrench is such that it may be easily supported on a table surface in a ready-to-use position. Because of the relationship between the body and knurled wheel of the wrench, the same fingers used to manipulate the wheel also, without additional effort, serve to guide and position the wrench. Should the wrench be canted as it is fitted upon the handpiece, damage which might otherwise occur because of misalignment during wrench rotation is avoided because of the automatically retractable mounting of the wrench shaft and tangs. The spring loading of the parts also insures that proper insertion of the shaft and tangs will occur when proper alignment is attained.

The danger of overtightening is eliminated or greatly reduced by forming the shaft as a torsion spring. The spring effect not only reduces overtightening because of the spring cushioning, but the onset of spring action signals the user when a proper degree of tightness has in fact been achieved.

In brief, the wrench comprises an angular C-shaped body with horizontally-projecting upper and lower arms and a vertical connection portion. The lower arm has a socket in its undersurface for receiving the head of a contra-angle handpiece. A burtube-chuck adjusting assembly is disposed between the arms and projects into the socket through a bore in the lower arm. The assembly includes a vertically-elongated spring shaft having a lower end portion of non-circular cross section which is normally disposed within the socket and is adapted to be received in an opening at the upper end of a handpiece chuck to lock the rod and chuck against independent relative rotation. At least one depending burtube-engaging lug also projects downwardly into the socket and is adapted to be received within an opening at the upper end of a handpiece burtube to lock the lug and burtube against independent relative rotation. The knurled operating wheel is rotatably mounted between the arms and is operatively connected either to the lug or to the shaft for rotating the member to which it is connected. Locking means are affixed to the upper end of the body and are connected to the other member (the lug or shaft to which the knurled wheel is not connected) for preventing rotation of that other member as the wheel is turned.

Dimensions of the parts are important because the wheel must be capable of being rotated between the thumb and index fingers of one hand while those fingers also engage the connecting portion of the body to stabilize and guide the wrench. In general, the knurled wheel should have a diameter within the range of about 5 to 25 millimeters, and the connecting portion of the body should have a thickness (measured normal to a plane parallel with the rotational axis of the wheel) substantially less than the diameter of that wheel. A size differential of at least three millimeters should be provided.

Both the lug-providing member and the shaft are spring-loaded so as to retract automatically until proper alignment is achieved. The shaft is of substantial length and, in a preferred form of the invention, is restrained against rotation by locking means engaging the upper portion of the shaft. Consequently, a substantial portion of the length of the spring shaft is free to twist as a collet chuck becomes tightened by rotation of the knurled wheel. Such flexure cushions the final tightening to prevent damage to the parts and also indicates to the user that proper tightening has been achieved.

Other advantages and objects of the invention will become apparent from the drawings and the detailed description of an illustrative embodiment.

DRAWINGS

FIG. 1 is a perspective view of a wrench embodying the invention, the wrench being illustrated in one of the positions it might be held during chuck adjustment of a handpiece.

FIG. 2 is an enlarged vertical sectional view taken generally along the line 2—2 of FIG. 1.

FIG. 2A is a fragmentary vertical sectional view showing the parts as they are illustrated in FIG. 2 but with the wrench fitted upon a dental handpiece.

FIG. 3 is an exploded perspective view of the wrench, it being noted that the main elements of the burtube and chuck adjusting assembly are illustrated to one side of the body of the wrench.

FIG. 4 is an enlarged end view taken along line 4—4 of FIG. 3.

FIG. 5 is an enlarged sectional view taken along line 5—5 of FIG. 3.

FIG. 6 is an enlarged fragmentary longitudinal sectional view of the lower portion of the chuck-restraining shaft.

FIG. 7 is a top plan view (in reduced scale) taken along line 7—7 of FIG. 2.

FIG. 8 is a bottom plan view taken along line 8—8 of FIG. 2 and presented in the same scale as FIG. 7.

FIG. 9 and 10 are elevational views drawn to the same scale as FIGS. 7 and 8 and taken along lines 9 and 10 of FIG. 2.

DESCRIPTION

FIG. 1 illustrates the wrench 10 as it is held in one hand to adjust the chuck of a contra-angle handpiece 11 held in the other. What is shown is simply one of several positions in which the wrench may be held for handpiece adjustment. Thus, the handpiece may, if desired, be held with the bur 12 facing upwardly, in which case the position of the wrench would also be reversed. Throughout the specification, for convenience in identifying the parts and their relationships, the wrench will be described with its handpiece-receiving socket facing downwardly as it might be fitted upon a handpiece with a downwardly-facing bur. It is to be understood, however, that terms such as "upper", "lower", "horizontal", and "vertical" are intended only to orient the parts of the wrench relative to each other and that the wrench as a whole may be oriented in any number of positions during use.

Wrench 10 comprises an angular integrally-formed C-shaped body 13 having a pair of horizontally-projecting upper and lower arms 14 and 15 integrated with a vertical connecting portion or strut 16. The upper surface 14a of arm 14, and the lower surface 15a of arm 15 are parallel, relatively large, and planar, the result being that the wrench may be supported in stable condition with either of its surfaces 14a or 15a resting upon a flat supporting surface. The arms also terminate at their free ends in planar end surfaces 14b and 15b that both lie in a plane perpendicular to the plane of strut 16 so that the wrench may also be supported in stable condition with those surfaces resting upon a flat support.

Lower arm 15 has a socket 16 extending upwardly from its undersurface for receiving the upper portion of an air-turbine contra-angle handpiece head 11a (FIGS. 1 and 2A). A bore 17 extends vertically through the lower arm, the bore being aligned and communicating with the downwardly-facing socket 16.

A burtube-chuck adjusting assembly, designated generally by the numeral 18 is disposed between the spaced arms and projects into the socket 16 through bore 17. As shown most clearly in FIGS. 2 and 3, the assembly includes a vertically-elongated shaft 19 of non-circular (preferably square) cross sectional configuration, a sleeve or bushing 20 which is fixed to the lower portion of the shaft and, in the particular illustration given, locking means in the form of a vertical reaction tube 21. The reaction tube has an intermediate portion 21a of cylindrical configuration, an upper portion 21b of non-circular (square) cross sectional configuration, and a lower end portion 21c which has a reduced external diameter and which has a non-circular (square) bore 22 therethrough. The bore is dimensioned to slidably receive shaft 19 while at the same time preventing independent relative rotation of the parts.

The non-circular upper end portion 21b of the reaction tube is received within a similarly-shaped opening 23 which extends through upper arm 14 in vertical alignment with bore 17 in the lower arm. Retaining means, shown in the drawings as a C-ring 24 received within annular groove 25 of the reaction tube, anchors the tube against upward movement with relation to upper arm 14.

Referring to FIG. 2, it will be seen that the reaction tube 21 and the chuck shaft 19 extend into the bore 26 of a vertically-elongated knurled cylindrical wheel or handle 27 disposed between the upper and lower arms. The lower end portion of the tubular wheel extends into bore 17 of the lower arm and a downwardly-facing shoulder 28 of the wheel bears against the top surface of that arm to limit the extent of the wheel's downward movement. The wheel is freely rotatable about the reaction tube 21 and shaft 19 and, since the vertical length of the wheel is substantially less than the distance between the upper and lower arms, the wheel may also be shifted upwardly into a raised position indicated in broken lines in FIG. 2. Helical compression spring 29, disposed within the bore of the wheel and interposed between the lower portion of the wheel and the reaction tube, performs the dual functions of urging the wheel into its normal lowered position illustrated in the drawings and of maintaining the non-circular upper end 21b of the reaction tube in the opening 23 of the upper arm 14.

At least one, and preferably a plurality, of lugs or tangs 30 project downwardly into socket 16 to engage recesses in the burtube or rotor of a dental handpiece upon which the wrench may be fitted. In the form depicted herein, the tangs project downwardly from the lower end of wheel 27 and are formed integrally with that wheel. A pair of such tangs are shown in the drawings, such tangs being diametrically disposed and spaced equidistant from the rotational axis of wheel 27.

Sleeve 20 and the lower end portion of shaft 19 extend downwardly through the reduced lower end 26a of the bore 26 of wheel 27. It is to be noted that the sleeve is fixed to the shaft slightly above the extreme lower end of that shaft, thereby exposing the extreme lower end or tip portion 19a of the shaft. The axial length of the exposed tip portion is such that the shaft, when it enters the noncircular opening 31 at the upper end of the chuck 32 of a dental handpiece, cannot reach or displace the shank of a bur 12 from that chuck (note space 32a in FIG. 2A). The lower end of sleeve 20, being larger than the opening in the chuck, serves as a stop to limit the extent of such penetration. It is also to be noted that the horizontal edges at the tip 19a of the shaft are slightly beveled or rounded (FIG. 6) to facilitate insertion of the tip into the opening of a handpiece chuck.

Sleeve 20 has an enlarged upper end 20a of greater diameter than the reduced lower portion of bore 26a, the upper end of the sleeve thereby limiting the extent of downward movement of the sleeve and shaft relative to wheel 27. A helical compression spring 33 extends about the shaft between the upper end of the sleeve and the lower end of reaction tube 21 to urge the sheathed shaft into the normally lowered position illustrated in FIG. 2.

Dimensions of the wrench are important because, among other things, the knurled wheel 27 should be received between and rotated by the same fingers which also grip the strut or connecting portion 16 of the frame (FIG. 1). the general, the outside diameter of the knurled wheel should fall within the range of about 5 to 25 millimeters. In what is believed to be a particularly effective embodiment, a diameter of about 9 to 10 millimeters has been used. The strut or connecting portion should have a thickness (measured normal to a plane parallel with the rotational axis of the handle) which is substantially less than the diameter of the handle. A differential of at least 3 millimeters has been found particularly effective. As shown most clearly in FIGS. 3 and 9, the connecting strut is generally planar in configuration, having a width (when measured along a plane parallel with the rotational axis of the handle or wheel) which is substantially greater than its thickness. A vertical edge 16a of the connecting strut is disposed in closely-spaced relation with respect to the handle wheel 27 (FIG. 2). In general, the spacing should not exceed 4 millimeters and preferably should be 2 millimeters or less. By reason of such dimensional relationships, an operator can readily grasp the wrench and rotate the wheel between the thumb and index fingers while using the same fingers to grip connecting strut 16 and thereby guide and control the wrench in its entirety. Because of the close spacing between the wheel and the strut, such manipulation may be performed without danger of pinching the operator's fingers between the parts.

In operation, the wrench is fitted upon the upper end of the head 11a of a contra-angle handpiece 11 as shown in FIGS. 1 and 2A. The parts are fixed against relative rotation by means of a semi-circular recess 34 which communicates with socket 16 and which extends through a wall portion of the lower arm in diametric opposition to the connecting strut 16. The recessed wall is fitted over the neck 11b of the handpiece in the manner illustrated.

When the handpiece head is fully inserted into the socket 16, shaft 19 is displaced upwardly into a partially raised position by reason of engagement between the upper end of the chuck 32 and the lower end of sleeve 20 (FIG. 2A). A secure interlock is thereby assured between the shaft and the chuck without, at the same time, causing the tip of the shaft to enter too deeply into the chuck and thereby displace the bur 12.

Tangs of lugs 30 are received within slots or openings 35 at the upper end of burtube (rotor) 36. Should it happen that the slots do not immediately register with the tangs, slight rotation of the handle wheel 27 will shift the tangs into position to be received in those slots. Until such alignment occurs, the tangs 30 and wheel 27 are displaced upwardly as indicated by the broken lines in FIG. 2. When registry is achieved, spring 29 urges the wheel and tangs downwardly into the operating positions illustrated in FIG. 2A.

Tightening or loosening of the chuck is accomplished by simply rotating the wheel 27 one direction or the other. In the use of the wrench shown in the drawings, shaft 19 holds the chuck 32 against rotation while tangs 30 turn the burtube 36 in the direction of rotation of the wheel 27. While the advantages of rotating the burtube about a stationary chuck are fully disclosed in the previously-identified co-pending application, it is believed apparent that the structure disclosed herein might be modified in keeping with the teachings of U.S. Pat. No. 3,325,899 to utilize the tangs for holding the burtube stationary while the wheel is rotated to turn the chuck.

The substantial vertical length of shaft 19, and the spring metal from which that shaft is formed, play an important role in the operation of the chuck. It will be observed that the reaction tube 21 connects to the shaft 19 near the upper end of that shaft, thereby allowing for a substantial length of shaft between the reaction tube and the beveled tip 19a. The length of shaft below the reaction tube serves as a torsion spring during operation of the wrench. As handle wheel 27 is rotated to commence the closing of the jaws of chuck 32 about the shank of a bur 12, the shaft 19 remains undeformed or untwisted; however, as the chuck's jaws become tightened upon the bur, the resistance against further relative rotation of the parts in response to continued torque applied to the finger wheel 27 tends to twist the elongated shaft. The effect to an operator of the wrench is generally a sensation of a cushioned blocking of further rotation of the wheel rather than an abrupt stopping action. The twisting action of the torsion shaft thereby signals the user when the parts of the handpiece are approaching optimum tightness and, in addition, reduces the possibility that overtightening, and possible damage associated therewith, might occur.

It is believed evident that the torsion shaft may be formed of any suitable metal having the requisite properties of strength and flexibility. The unitary body 13 of the wrench may be formed of any suitable material, although tough plastic materials such as polycarbonates have been found especially effective.

While in the foregoing we have disclosed an embodiment of the invention in considerable detail for purposes of illustration, it will be understood by those skilled in the art that many of these details may be varied without departing from the spirit and scope of the invention.

We claim:

1. A wrench for contra-angle handpieces comprising a C-shaped body having horizontally-projecting upper and lower arms and a vertical connecting strut therebetween; said lower arm having a socket in its undersurface for receiving the upper portion of a contra-angle handpiece head and having a vertical bore extending through said lower arm and communicating with said socket; a burtube-chuck adjusting assembly disposed between said arms and projecting into said socket through said bore; said assembly including a vertically-elongated shaft member having a lower end portion of non-circular cross sectional configuration normally disposed within said socket and adapted to be received in an opening at the upper end of a handpiece chuck to lock said shaft member and chuck against independent relative rotation about the axis of the shaft member; at least one depending burtube-engaging lug member normally projecting downwardly into said socket and adapted to be received within an opening at the upper end of a handpiece burtube to lock said lug member and burtube against independent relative rotation about the axis of said shaft member; a generally cylindrical handle wheel rotatably mounted between said arms and operatively connected to one of said lug and shaft members for rotating said one member about said axis; and locking means affixed to said upper arm and connected to the other of said members for preventing rotation of said other of said members about the axis of said shaft member; said generally cylindrical handle wheel having a diameter within the range of about 5 to 25 millimeters; said vertical connecting strut having a thickness, measured normal to a plane parallel with the axis of said shaft member, substantially less than the diameter of said handle wheel.

2. The wrench of claim 1 in which said connecting strut has a thickness at least 3 millimeters less than the diameter of said handle wheel.

3. The wrench of claim 2 in which said connecting strut is generally planar in configuration and has a width, measured along a plane parallel with the axis of said shaft member, substantially greater than the thickness of said strut.

4. The wrench of claim 3 in which said connecting strut has a vertical edge in closely-spaced relation relative to said handle wheel.

5. The wrench of claim 4 in which the spacing between said vertical edge and said handle wheel does not exceed about 4 millimeters.

6. The wrench of claim 4 in which said spacing does not exceed approximately 2 millimeters.

7. The wrench of claim 1 in which said body is formed of rigid plastic material.

8. The wrench of claim 1 in which said upper and lower arms of said body have generally flat upper and lower surfaces, respectively; whereby, said wrench may be supported in stable condition with either said upper surface or said lower surface resting upon a horizontal support.

9. The wrench of claim 1 in which said upper and lower arms terminate at their free ends in planar end surfaces that lie in a single plane generally perpendicular to said connecting strut; whereby, said wrench may be supported in stable condition with said end surfaces resting upon a generally horizontal support surface.

10. The wrench of claim 1 in which said lower arm is provided with a recess communicating with said socket and extending through a wall portion of said arm disposed in diametric opposition to said connecting strut for receiving the neck portion of a contra-angle handpiece upon which said wrench is fitted.

11. The wrench of claim 1 in which said C-shaped body is integrally formed.

12. The wrench of claim 1 in which said shaft and lug members are mounted upon said body for limited axial movement relative thereto.

13. The wrench of claim 12 in which said shaft member is mounted for limited vertical movement independent of said lug member.

14. The wrench of claim 12 in which spring means are provided for urging said shaft and lug members downwardly relative to said body.

15. The wrench of claim 1 in which said shaft member includes a downwardly-facing annular shoulder defining the upper limit of said shaft member's lower end portion; said shoulder being engagable with the top surface of a handpiece chuck for limiting the extent of insertion of said lower end portion into the opening of said chuck.

16. The wrench of claim 1 in which said other of said members comprises said shaft member.

17. The wrench of claim 16 in which said elongated shaft member is formed of spring metal and said locking means is connected to said shaft member at a substantial distance above said shaft member's lower end portion to provide a substantial length of said shaft member between said locking means and a handpiece chuck for torsional spring cushioning of the tightening force manually applied by relative rotation of said handle wheel and a burtube coupled thereto by said lug member.

18. A chuck wrench for contra-angle dental handpieces comprising a C-shaped body having spaced upper and lower horizontal arms joined by a connecting strut; said lower arm having a socket provided in its undersurface for receiving the head portion of a contra-angle handpiece and having a vertical bore extending therethrough and communicating with said socket; a burtube-chuck adjusting assembly disposed between said arms and projecting into said socket through said bore; said assembly including a vertically-elongated torsion spring shaft having a lower tip portion of non-circular cross section normally disposed within said socket and adapted to be received in an opening at the upper end of a handpiece chuck for locking said shaft and chuck against independent relative rotation; means engaging the upper portion of said torsion spring shaft to lock the same against rotation relative to said upper arm; and a vertically-elongated handle wheel having a rotational axis coincident with the axis of said shaft and mounted for rotation there-about; said wheel being disposed between said arms and having at least one depending lug normally projecting downwardly into said socket and adapted to be received within an opening at the upper end of a handpiece burtube for locking said wheel and burtube against independent relative rotation; said elongated spring shaft having a substantial portion of the length thereof disposed between said tip and said means to provide torsion spring action for indicating when proper tightening torque is approached and for protecting a handpiece against overtightening of its chuck.

19. The wrench of claim 18 in which said lower arm is also provided with a wall portion having a semicircular recess communicating with said socket in diametric opposition to said strut, said recess being adapted to receive the neck portion of a contra-angle handpiece upon which said wrench is fitted.

20. The wrench of claim 18 in which said shaft and wheel are mounted for limited axial movement relative to said body.

21. The wrench of claim 20 in which said shaft is mounted for limited vertical movement independent of said wheel.

22. The wrench of claim 18 in which said shaft is provided with a downwardly-facing annular shoulder at the upper limit of said tip portion, said shoulder being engageable with top surface of a handpiece chuck for limiting the extent of insertion of said tip portion into the opening of said chuck.

23. The wrench of claim 18 in which said means comprises a vertical reaction tube having an upper end fixed against rotation relative to said upper arm and having a lower end defining a non-circular bore slidably receiving the upper portion of said shaft.

24. The wrench of claim 23 in which a sleeve is secured to the lower portion of said shaft; a compression spring being disposed between said sleeve and said reaction tube for urging said shaft into a normally lowered position.

25. The wrench of claim 23 in which said reaction tube is provided with a cylindrical outer surface; said wheel being slidably and rotatably mounted upon said cylindrical surface of said reaction tube; and spring means cooperating with said reaction tube and said wheel for urging said wheel downwardly into a normally lowered position.

* * * * *